(12) United States Patent
Schermer et al.

(10) Patent No.: US 7,413,893 B2
(45) Date of Patent: Aug. 19, 2008

(54) METHODS, APPARATUS AND COMPOSITIONS FOR IMPROVED MEASUREMENTS WITH OPTICAL BIOSENSORS

(75) Inventors: Mack J. Schermer, Belmont, MA (US); Mark Norman Bobrow, Lexington, MA (US); Philip R. Buzby, Brockton, MA (US); Thomas R. Mullinax, Newton, MA (US)

(73) Assignee: PerkinElmer LAS, Inc., Waltham, MA (US)

( * ) Notice: Subject to any disclaimer, the term of this patent is extended or adjusted under 35 U.S.C. 154(b) by 681 days.

(21) Appl. No.: 10/864,086

(22) Filed: Jun. 9, 2004

(65) Prior Publication Data

US 2005/0272046 A1    Dec. 8, 2005

Related U.S. Application Data

(60) Provisional application No. 60/320,257, filed on Jun. 9, 2003.

(51) Int. Cl.
*C12Q 1/68* (2006.01)
*C12M 1/34* (2006.01)

(52) U.S. Cl. .............. 435/287.2; 435/6; 435/288.7; 422/82.06; 436/164

(58) Field of Classification Search .......... 422/82.06; 435/6, 288.4, 288.2, 289.1, 288.7, 287.2, 435/808; 436/164
See application file for complete search history.

(56) References Cited

U.S. PATENT DOCUMENTS

| | | | |
|---|---|---|---|
| 5,196,306 A * | 3/1993 | Bobrow et al. .......... 435/7.9 |
| 5,221,448 A * | 6/1993 | Weinberger et al. ....... 204/452 |
| 5,726,064 A * | 3/1998 | Robinson et al. ......... 436/514 |
| 6,377,721 B1* | 4/2002 | Walt et al. .............. 385/12 |
| 6,416,951 B1* | 7/2002 | Schmidt et al. ............ 435/6 |
| 6,471,910 B1* | 10/2002 | Haggard et al. .......... 264/555 |
| 6,734,956 B2* | 5/2004 | Byrne et al. ............. 356/128 |
| 2003/0148542 A1* | 8/2003 | Pawlak et al. ........... 436/518 |
| 2003/0207290 A1* | 11/2003 | Kenten et al. .............. 435/6 |

FOREIGN PATENT DOCUMENTS

WO    WO01/01112    *    1/2001

* cited by examiner

*Primary Examiner*—Walter D. Griffin
*Assistant Examiner*—Shanta G Doe

(57) ABSTRACT

The invention provides an apparatus for interrogating an optical biosensor. The apparatus includes (a) locating means for positioning one or more optical biosensors; (b) calibration means for generating a reference measurement; (c) one or more biosensors for generating one or more sample measurements, the biosensors being substantially planar and removable from the apparatus; (d) a reading means for interrogating biosensor and calibration means, and (e) a transport means for moving one or more of a biosensor, the calibration means and the reading means, whereby the reading means is positioned to interrogate the biosensor and the calibration means.

19 Claims, 4 Drawing Sheets

METHODS, APPARATUS AND COMPOSITIONS FOR IMPROVED MEASUREMENTS WITH OPTICAL BIOSENSORS

This application claims the benefit of priority to U.S. Provisional Application Ser. No. 60/320,257, filed on Jun. 9, 2003, which is incorporated herein by reference.

SUMMARY OF THE INVENTION

The invention provides an apparatus for interrogating an optical biosensor. The apparatus includes (a) locating means for positioning one or more optical biosensors; (b) calibration means for generating a reference measurement; (c) one or more biosensors for generating one or more sample measurements, the biosensors being substantially planar and removable from the apparatus; (d) a reading means for interrogating biosensor and calibration means, and (e) a transport means for moving one or more of a biosensor, the calibration means and the reading means, whereby the reading means is positioned to interrogate the biosensor and the calibration means. In an embodiment, the apparatus also includes a computational means capable of determining a corrected measurement from a reference measurement and sample measurement. In another embodiment, the reading means comprises a plurality of interrogating elements operating in parallel. In a further embodiment, the calibration means is attached to a support structure of one or more biosensors. The support structure can be, for example, a microplate, and the calibration means can be located within the microplate. The calibration means also can be incorporated into a measuring apparatus.

The invention provides a method for interrogating an optical biosensor. The method involves (a) generating a reference measurement using a calibration means; (b) generating one or more sample measurements using one or more biosensors, the biosensors being substantially planar and removable from the apparatus; (c) determining a corrected measurement, whereby the reference and sample measurements are generated by a reading means positioned to interrogate the calibration means and the biosensor. In an embodiment, the corrected measurement is the difference between the reference measurement and the sample measurement.

Also provided by the invention is a method for measuring multiple signals from locations on an optical biosensor. The method involves (a) imaging a field of interest on an optical biosensor, wherein the optical biosensor is substantially planar, and wherein the imaging is performed using means other than an optical biosensor; (b) determining planar coordinates of locations of interest based on the resulting image; and (c) interrogating the optical biosensor at the locations of interest. In an embodiment, the optical biosensor is a microarray substrate. In another embodiment, the optical biosensor is an electrophoresis substrate. In a further embodiment, the imaging detects a property selected from diffuse reflection, contrasting color, transmission, absorption, scatter, fluorescence and chemiluminescence from either the assay materials or from the substrate.

The invention provides another apparatus for interrogating an optical biosensor. The apparatus includes (a) locating means for positioning an optical biosensor, the biosensor being substantially planar and removable from the apparatus; (b) reading means for determining locations of interest on the optical biosensor; (c) imaging means for producing an electronic image of a field of the optical biosensor, the field being large compared to the locations of interest; (d) computing means for determining the coordinates of locations of interest; and (e) transport means for moving either or both the biosensor and reading means, whereby the locations of interest are interrogated.

Also provided by the invention are methods for increasing a signal generated by a biosensor. In one embodiment, the method involves binding an entity of known mass to an analyte contained in a sample. In another embodiment, the method involves using catalyzed reporter deposition.

Further provided by the invention is a microplate biosensor apparatus. The apparatus includes a plurality of wells, a surface of each well including (a) a biosensor area that produces a composite signal corresponding to a target molecule and a reference sample, wherein a relatively higher proportion of the biosensor area signal corresponds to the target molecule, and (b) a reference sensor area that produces a composite signal corresponding to the target molecule and the reference sample, wherein a relatively higher proportion the reference area signal corresponds to the reference sample.

The invention provides an optical biosensor measuring apparatus. The apparatus includes (a) locating means for locating optical biosensor structures in a microplate; (b) reading means for interrogating the located optical biosensors; and (c) reference sensor means for measuring the refractive index of reference sample in the wells of the microplate. In an embodiment, the apparatus also includes transport means for moving any of the reading means, the reference sensor or the microplate structure to allow each well of the microplate structure to be addressed by the reading means and the reference sensor.

The invention also provides a method for compensating for changes in the optical properties of reference sample and sensors during an optical biosensor assay. The method involves (a) contacting one or more wells of a biosensor microplate with reference sample; (b) determining a first biosensor reference signal from a well containing reference sample only; (c) adding one or more samples to the remaining wells in the microplate; (d) allowing the sample to incubate to the desired state; (e) determining a second biosensor reference signal from the well containing reference sample only; (f) determining a biosensor assay signal from one or more sample wells; and (g) determining corrected values of the assay signals based on the difference between the first and the second reference signals.

Further provided by the invention is a method for obtaining two measurements from a single location on a resonant reflective biosensor wherein the biosensor is interrogated with light of each of two orthogonal linear polarizations. In one embodiment, the two measurements are used to determine binding of a target molecule to the biosensor.

The invention provides an apparatus for obtaining measurements from a resonant reflective biosensor. The apparatus includes a reading means that can interrogate the biosensor with light at each of two orthogonal linear polarizations.

The invention also provides a method for performing labelless assays on hydrophobic compounds using an optical biosensor wherein the reference sample comprises a water-miscible organic solvent. In one embodiment, the hydrophobic compounds are hydrophobic proteins.

The invention further provides a method for measuring the optical absorbance of the sample and reference sample in a resonant reflective biosensor. The method involves (a) interrogating the biosensor with broadband light; (b) reading the reflected biosensor signal at a first band of resonance wavelengths with first reading means; (c) placing wavelength selecting means in the path of the transmitted broadband light, the selecting means configured to pass a second transmitted wavelength band that does not coincide with the resonant reflective band; (d) reading the relative power of the second band with second reading means; and (e) determining the optical absorbance of the sample and reference sample at the second wavelength band.

In addition, the invention provides a method for improving the spectral peak resolution of a resonant reflective biosensor. The method involves (a) determining two or more reference spectra from a sample quantity of biosensors on a high-resolution spectrometer; (b) characterizing the reference spectra with an algorithm or equation; (c) obtaining one or more assay spectra from a biosensor using a low-resolution spectrometer; and (d) determining reflectance spectrum peaks of the assay spectra by interpolating along the curve defined by the algorithm or equation.

Further provided by the invention is method of interrogating a resonant reflective biosensor at two wavelengths. In the method, a first wavelength generates a signal relatively more sensitive to a target molecule and a second wavelength generates a signal relatively more sensitive to the reference sample.

The invention provides an apparatus for performing real-time detection of an amplified target nucleic acid. The apparatus includes (a) a capillary tube; (b) temperature control means that controls the temperature of three of more segments of the capillary tube wherein each segment contains zones maintained at three or more selected temperatures; (c) means for moving a sample to the various temperature zones; and (d) a biosensor configured to measure the amount of nucleic acid in the sample. In an embodiment, the biosensor is an optical biosensor. In another embodiment, the capillary is formed into a serpentine shape comprising a serially connected plurality of repeated elements, each element having three or more temperature-controlled zones and a biosensor.

In addition, the invention provides a method of determining an amount of a target nucleic acid. The method involves (a) introducing a sample into a capillary tube, the sample suspected of containing a target nucleic acid, wherein the sample comprises a polymerase enzyme, one or more primers and nucleotides; (b) controlling the temperature of three of more segments of the capillary tube wherein each segment contains zones maintained at three or more selected temperatures; (c) moving the sample through the tube, whereby the target nucleic acid, if present, is amplified by the polymerase enzyme; and (d) determining an amount of the target nucleic acid using a biosensor. In one embodiment, the capillary tube has a serpentine shape comprising a serially connected plurality of repeated elements, each element comprising three temperature-controlled zones and a biosensor.

BRIEF DESCRIPTION OF THE DRAWINGS

FIG. 4a is a top-oblique view of the microplate. FIG. 4b is a bottom-view detail of a corner of the plate, showing a reference sensor mounted in the skirt area.

DETAILED DESCRIPTION OF THE INVENTION

Figure 1:
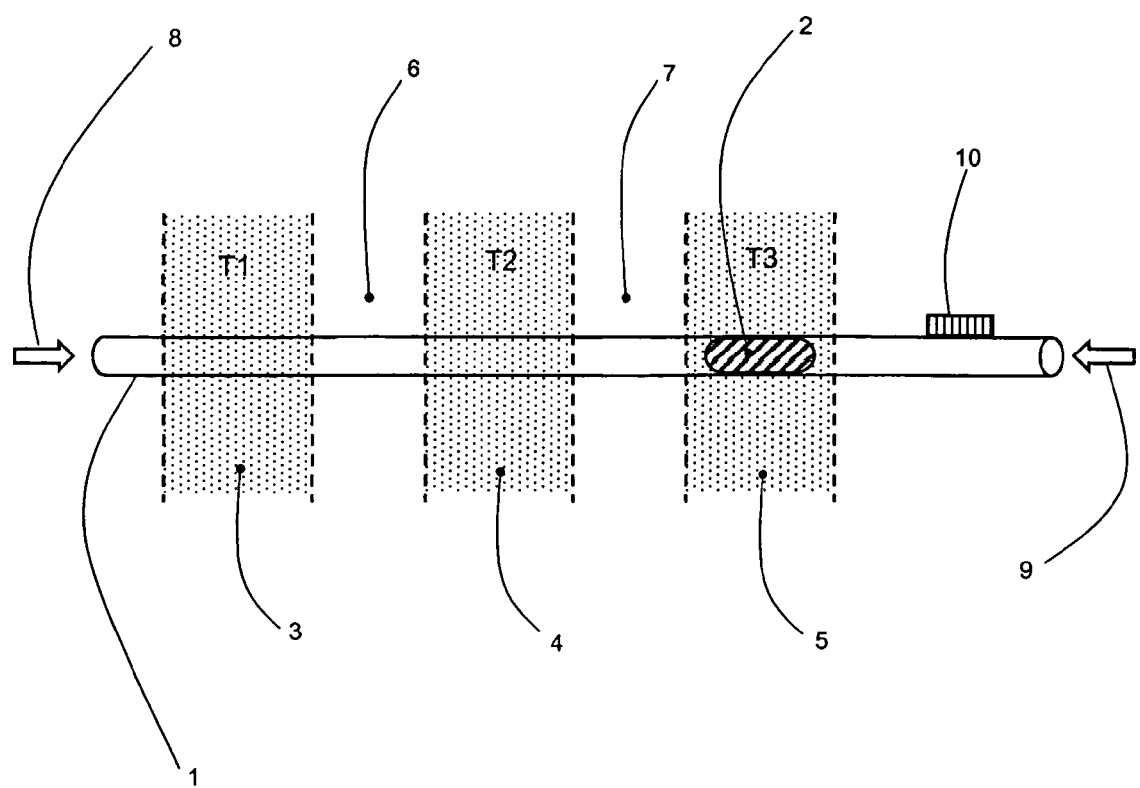
FIG. 1 shows a schematic drawing of one embodiment of an apparatus for performing real-time detection of an amplified target nucleic acid.

The present invention relates to biosensors and optical biosensors, to methods for improving measurements from optical biosensors, and to various apparatus for implementing the methods.

In one aspect, the invention provides improved biosensor apparatus and methods that provide increased sensitivity and accuracy by reducing artifacts caused by sensor draft, instrument drift and media effects.

In another aspect, the invention provides biosensor apparatus and methods for amplification and detection of a target nucleic acid using real-time PCR.

An apparatus of the invention can include one or more biosensors. A biosensor is an analytical device that links a specific biological element that creates a recognition event with a physical element that transduces the recognition event. The detector can be sensitive to almost any type of physical parameter-electrical phenomena (current, potential, impedance), mass, temperature, and the intensity and phase of electromagnetic radiation, such as visible light. A specific type of biosensor useful in an apparatus of the invention is an optical biosensor. Optical biosensors and methods for their use have been described in U.S. Pat. Nos. 4,815,843 and 6,335,793 and U.S. patent application publications 2002-0127565, 2003-0027327, 2003-0027328, 2003-0032039, 2003-0068657, 2003-0059855, and 2003-0077660, which are incorporated herein by reference.

An exemplary optical change that can be determined using an optical biosensor is a change in the refractive index of a sample. Refractive index changes measured by an optical biosensor can be correlated to molecules binding to the surface of the sensor and to changes in the properties of the surrounding media. In practice, the signal components generated by changes in the surrounding media can be much larger than signal components generated by changes to the assay components immobilized on the sensor surface. It is one of the objects of the present invention to improve the discrimination between changes in the population of immobilized molecules and changes in the media.

Known optical biosensor systems can measure changes in the composite refractive index of materials in contact with or in the immediate vicinity of the sensor. It is an aspect of the present invention to measure the absolute refractive index of media and to indicate the index to the instrument user. The absolute index can be determined by calibrating biosensors to multiple solutions of known index or to a calibration standard incorporated into the instrument.

Optical biosensors are interrogated by directing optical energy, generally in the form of an approximately collimated beam of light, at the sensor. Interrogating also can include detection and measurement, which can performed by reading some property of the light reflected or re-emitted by the sensor, a wavelength spectrum, a wavelength, a power, a light propagation angle, or the positions of fringe images in an interference pattern for example. In resonant reflective biosensors the biosensor is interrogated by directing a collimated beam of broadband light at its surface. A narrow band of light is reflected, and the spectrum of the reflected light is the signal. The reflected spectrum is measured and the data processed to determine its peak wavelength which is correlated to the refractive index at and near the surface of the biosensor.

The signals generated by typical optical biosensors can drift over time due to either sensor drift or instrument drift with no change in assay composition. Further, optical biosensor detection instruments can incorporate multiple signal reading or signal processing components that can not be exactly calibrated with each other to produce the same signal from the same assay. The multiple reading or processing components can also drift with respect to one another over time. As the biosensor measurements cannot be more precise than the reproducibility of the reading and processing elements, typical biosensors fall short of providing a desired level of sensitivity.

According to the present invention, a calibration element is incorporated into the assay reading instrument to advantageously minimize or eliminate variations between sensors and from any one sensor over time. The calibration element is preferably a robust time-invariant implementation of the optical biosensor, mounted in the instrument in such a way that each reading component of the instrument can obtain a calibration signal from the single calibration element. The calibration element can be, for example, a micro-machined glass or silicon grating with similar signal generating properties as the mass-produced and more variable plastic biosensors used for assays. The calibration element can be incorporated into the structure of the removable set of biosensors, such as in the support structure of a biosensor microplate not coincident with any of the wells of the microplate, if desired.

The invention provides an apparatus for interrogating an optical biosensor. The apparatus includes (a) locating means for positioning one or more optical biosensors; (b) calibration means for generating a reference measurement; (c) one or more biosensors for generating one or more sample measurements, the biosensors being substantially planar and removable from the apparatus; (d) a reading means for interrogating biosensor and calibration means, and (e) a transport means for moving one or more of a biosensor, the calibration means and the reading means, whereby the reading means is positioned to interrogate the biosensor and the calibration means. In an embodiment, the apparatus also includes a computational means capable of determining a corrected measurement from a reference measurement and sample measurement. In another embodiment, the reading means comprises a plurality of interrogating elements operating in parallel. In a further embodiment, the calibration means is attached to a support structure of one or more biosensors. The support structure can be, for example, a microplate, and the calibration means can be located within the microplate. The calibration means also can be incorporated into a measuring apparatus.

Figure 3:
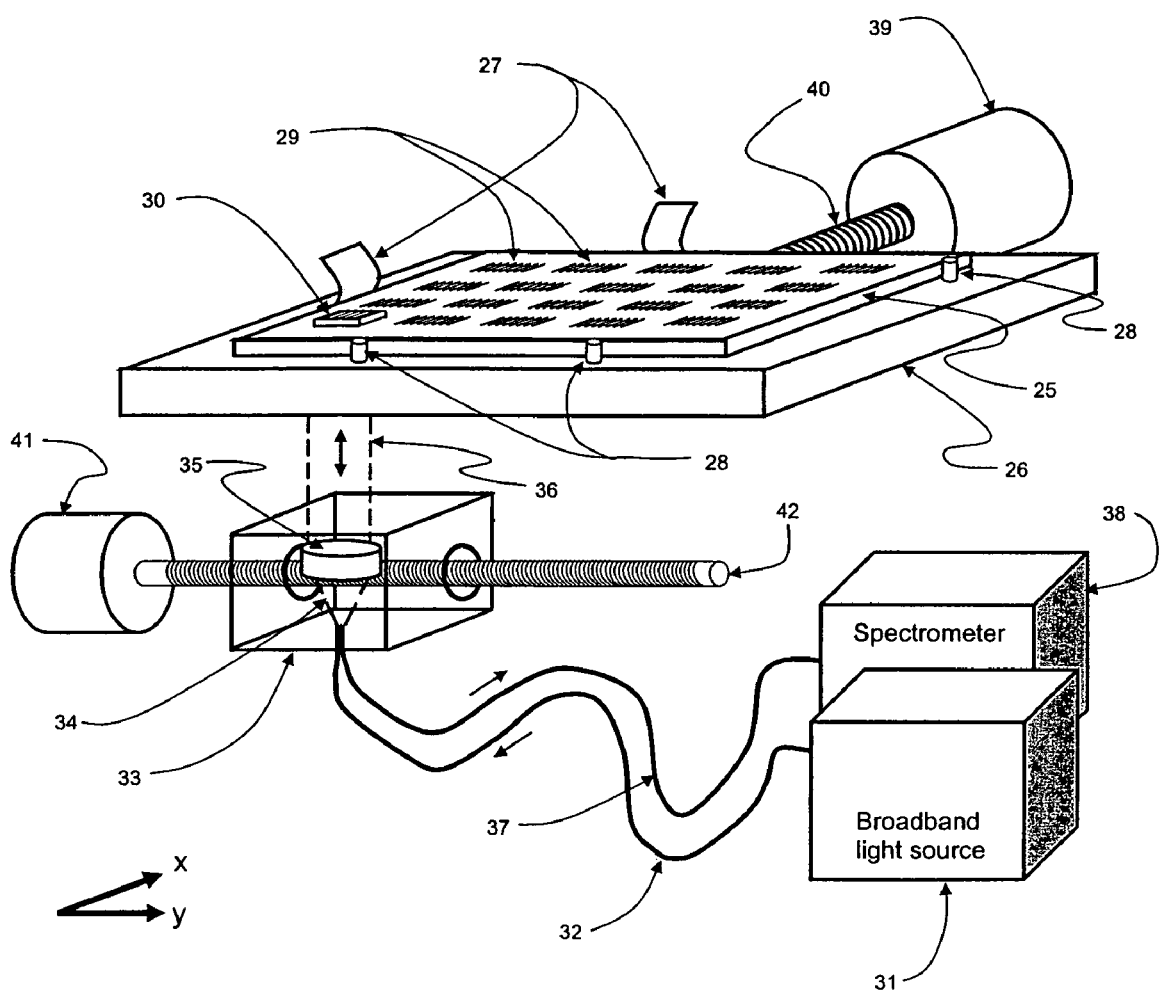
FIG. 3 shows a schematic drawing of one embodiment of an apparatus of the invention for interrogating an optical biosensor.

FIG. 3 shows a schematic drawing of an apparatus for interrogating an optical biosensor. A planar support 25 has a pattern of biosensor gratings 29 on its surface. The sensor areas could be in discreet locations as shown, or the entire surface can be a sensor where the biosensor detection can be done via imaging. The support can be made of plastic, glass, ceramic, or other rigid or semi-rigid material. The biosensors can be gratings, resonant reflective colorimetric sensors, or other forms. The substrate 25 is held in position on a detection stage 26 by locating means shown here as pins 28 and spring clips 27. The spring clips hold the substrate securely against the rigid datum surfaces provided by the pins and the stage.

The stage 26 is moveable in the X direction by a motor 39 and a leadscrew 40, connected to a nut on the stage (nut not shown). This mechanism provides biosensor interrogation addressability in the X direction.

Beneath the stage is the biosensor interrogation mechanism. The figure depicts an optical system for a colorimetric resonant reflective biosensor but the principles of the invention apply to a wide variety of biosensor types. A broadband light source 31 produces interrogation light spanning a range of wavelengths utilized by the biosensor. An illumination fiber optic 32, with slack to accommodate motion, brings the interrogation light to a read head 33. Interrogation light 34 exits the fiber as from a point source and enters a beamforming optic, shown here as a collimating lens 35. A collimated broadband interrogation beam 36 exits the read head upward toward the biosensor substrate.

The resonant reflective biosensor element reflects a narrow spectrum from the broadband interrogation. When interrogated at normal incidence as shown this reflected signal light travels back into the collimating lens along the same path as the interrogation beam 36; the two beams are congruent but traveling in opposite directions. The collimating lens focuses the signal light back to a point and a second signal fiber 37 receives it. The signal light propagates through the signal fiber 37 into a detection spectrometer 38. The spectrometer produces the spectrum of the signal light, from which a characteristic signal wavelength can be derived. This characteristic wavelength is the signal from a calorimetric resonant biosensor system.

The read head 33 is moveable in the Y direction, moved by motor 41 and leadscrew 42. While FIG. 3 shows the biosensor to be moveable in one direction and the read head in the other, any combination of moveable components that provides X-Y addressability of the biosensor substrate to the read head optics would perform the same function.

A reference biosensor 30 is shown mounted on top of the biosensor substrate 25. The reference biosensor element can incorporate at least one of the following characteristics in order to provide its referencing function. First, the reference sensor can be mounted such that it does not come in contact with the liquid assay reagents. If, for example, the biosensor is used in a planar microarray format where sample reagent is flooded over the entire surface, the reference sensor can be raised up from the sensor surface (as shown). Alternately, it can be on the bottom surface, masked, or held apart from the biosensor surface in some other manner. Second, the reference sensor can be constructed to be less prone to drift with temperature or other environmental factors. For example, if the biosensors are gratings constructed by using the low-cost method of replicating UV-cured epoxy on top of the substrate those gratings will change their resonance point as they absorb moisture, from ambient humidity or from the assay. The reference sensor could then be made of glass with a bulk-index doping grating or photoresist grating that is much less sensitive to moisture, for example.

Exemplary locating means for positioning one or more optical biosensors include a holder as part of a reading instrument that would, for example, locate a biosensor incorporated into a vial, microplate, or microarray substrate by means of clamping or spring loading.

Exemplary calibration means for generating a reference measurement include a replica of said biosensor, where the calibration element is constructed to generate signals an a manner less prone to drift with time or temperature than the sensing biosensors. For example, in the case of biosensors made with gratings, the calibration means may be made on a relatively stable but more expensive glass substrate in contrast to less expensive but less stable plastic substrates for the sensing biosensors.

Exemplary biosensors for generating one or more sample measurements include evanescent wave sensors, including grating-coupled waveguide sensors, interferometric waveguide sensors, resonant reflective colorimetric sensors, surface plasmon resonant (SPR) sensors, and the like.

Exemplary reading means for interrogating biosensor and calibration means include monochromatic collimated light beams, where the angle of a grating-outcoupled beam is measured; split coherent or partially coherent beams coupled into and out of a dual-path interferometric sensor with an interferogram detector; polychromatic collimated light beams reflected from a calorimetric resonant sensor with a spectrometer device for detecting; and the like.

Exemplary transport means for moving one or more of a biosensor, the calibration means and the reading means, such that the reading means is positioned to interrogate the biosensor and the calibration means, include a position-addressable motion stage, such as a single-axis or a two-axis X-Y stage that can be moved with stepper motors or servo motors, coupled to a linear stage with leadscrews, belt drives etc.; linear servo motors, or the like; with or without position sensing encoder means such as an optical rotary encoder or a linear grating encoder.

The invention provides a method for interrogating an optical biosensor. The method involves (a) generating a reference measurement using a calibration means; (b) generating one or more sample measurements using one or more biosensors, the biosensors being substantially planar and removable from the apparatus; (c) determining a corrected measurement, whereby the reference and sample measurements are generated by a reading means positioned to interrogate the calibration means and the biosensor. In an embodiment, the corrected measurement is the difference between the reference measurement and the sample measurement.

Known optical biosensors configured to perform assays on microarray substrates read signals from each pixel (picture element) in a area on the substrate that is known to support the microarray elements or spots of interest. The pixels read by the biosensor reading instrument are smaller than the microarray spots so that the instrument reads a number of signals that greatly exceeds the number of microarray spots. As the signal acquisition time and subsequent data processing time is considerable, it would be advantageous to reduce the number of biosensor signal readings taken to approximately the same value as the number of microarray spots. One aspect of the present invention is to optically image the area of interest of the microarray prior to measuring with the biosensor.

Therefore, the invention provides a method for measuring multiple signals from locations on an optical biosensor. The method involves (a) imaging a field of interest on an optical biosensor, wherein the optical biosensor is substantially planar, and wherein the imaging is performed using means other than an optical biosensor; (b) determining planar coordinates of locations of interest based on the resulting image; and (c) interrogating the optical biosensor at the locations of interest. In an embodiment, the optical biosensor is a microarray substrate. In another embodiment, the optical biosensor is an electrophoresis substrate. In a further embodiment, the imaging detects a property selected from diffuse reflection, contrasting color, transmission, absorption, scatter, fluorescence and chemiluminescence from either the assay materials or from the substrate.

Methods for imaging a field of interest on an optical biosensor using means other than an optical biosensing means include optical transmission (absorption) or reflection, using UV, visible, or near IR light to with a pixel size (resolution) significantly smaller than the nominal diameter of microarray spots, for example.

Methods for determining planar coordinates of locations of interest based on the resulting image include standard microarray spot-finding methods, including those based on projections, correlation, neural-net algorithms, or even manual-visual alignment.

Methods for interrogating an optical biosensor at a location of interest include imaging modalities for label-less detection, such as calorimetric resonant reflection or imaging SPR.

By finding the areas of interest (e.g., microarray spots) using conventional optical imaging at relatively high resolution and performing spot finding, the label-less biosensor interrogation can be done at very low resolution, e.g. one data point per microarray spot (or, in other words, with an interrogation beam approximately the same size as the microarray spot), requiring a simpler biosensor instrument that has much higher throughput.

The invention provides an apparatus for interrogating an optical biosensor. The apparatus includes (a) locating means for positioning an optical biosensor, the biosensor being substantially planar and removable from the apparatus; (b) reading means for determining locations of interest on the optical biosensor; (c) imaging means for producing an electronic image of a field of the optical biosensor, the field being large compared to the locations of interest; (d) computing means for determining the coordinates of locations of interest; and (e) transport means for moving either or both the biosensor and reading means, whereby the locations of interest are interrogated.

Imaging modalities can include reflection, scatter, fluorescence, chemiluminescence etc. with pixel resolutions smaller than the microarray spots, with the imaging performed in such a manner that the microarray spots can be distinguished from the background areas between spots. In the present invention the electronic image so produced is analyzed to determine the locations of the microarray spots of interest. One or more optical biosensors with sensing areas similar to (but not larger than) a microarray spot, in turn, are directed to measure the microarray spots at the locations. This process generates one optical biosensor measurement per microarray spot rather than a biosensor image of the entire microarray area. The biosensor optics and data processing are greatly simplified. This approach can also be used on sample substrates other than microarrays such as membranes, gels and the like.

Exemplary imaging means for producing an electronic image of a field of the optical biosensor include imaging resonant reflective calorimetric biosensors, imaging SPR.

Also provided by the invention are methods for increasing a signal generated by a biosensor. In one embodiment, the method involves binding an entity of known mass to an analyte contained in a sample.

Binding an entity of known mass to an analyte contained in a sample can be performed, for example, when molecules with mass similar to or larger than the specific binding pair are bound to a member of the pair in a process similar to conventional labeling. The mass label molecule is chosen for ease and uniformity of binding and does not require the conventional signal-generating aspects of a fluorescent, radioactive, chromogenic, chemiluminescent etc. label. Addition of mass to the binding pair increases the signal from any mass-detecting biosensor, including optical biosensors that detect changes in the composite refractive of the materials in close proximity, especially the contribution of the refractive index of bound molecules that is in approximate proportion to their density.

In another embodiment, the method for increasing a signal generated by a biosensor involves using catalyzed reporter deposition, such as the enzymatic labeling method Tyramide signal amplification (TSA), as a mechanism for binding mass labels. Catalyzed reporter deposition (CARD) is a method of signal amplification which constitutes the subject matter of U.S. Pat. Nos. 5,731,158, 5,583,001 and 5,196,306. It is also discussed in Bobrow et al., *Journal of Immunological Methods*, 125: 279-285 (1989) and in Bobrow et al., *Journal of Immunological Methods*, 137:103-112 (1991).

As the refractive index of the media can generate optical biosensor signals that are large compared to those generated by binding or functional events on the molecules immobilized onto the biosensor it is advantageous to distinguish the two effects. One aspect of the present invention is to provide two or more biosensor elements per assay sample, such as a microplate well. This can be implemented in several ways depending on the application. As one exemplary implementation, the assay biosensor with its immobilized binding pair members is incorporated into the microplate well. A second optical biosensor without immobilized members is inserted into the media from the top of the well. The second sensor measures the index of refraction of the media and any dissolved sample only, while the first sensor measures the composite signal of the immobilized binding pair plus the media. A third signal of the binding pair only can be derived from the first two. The second sensor can be of the same or different type than the first, and the reading instrument can incorporate washing means to wash the second sensor to reduce carryover between insertions into microplate wells.

In another implementation, the second sensor can also be incorporated into the microplate well, where the second sensor is configured to be relatively more sensitive to media refractive index than to bound molecule refractive index. This can be done by masking the second sensor from coating with the immobilized binding pair member, for example. In another implementation with grating-based optical biosensor both biosensors are coated, but the grating geometry of the two sensors is such that the first sensor is more sensitive to the near field (bound molecules) and the second sensor more sensitive to far field effects (the media). The two optical biosensors can also be interrogated with two different wavelength ranges. In the case of a resonant reflective biosensor, a single biosensor element can be interrogated with two different wavelength ranges, where the second wavelength range is directed at the biosensor at a second angle. Yet another implementation is to utilize a single grating biosensor element but interrogate it with two orthogonal linear polarizations of light, each polarization producing a signal with different relative sensitivities to the bound molecules and the media.

In assays where the assay signal is relatively small it is advantageous to compensate for changes in the biosensor and the media over the time required for assay completion. The term media refers to a reference sample or control sample, such as a liquid lacking a test sample but containing the same or similar components as the liquid in which a test sample is contained. In microplate optical biosensor assays it is one aspect of the present invention to use one or more of the microplate wells as reference sensors. In this implementation the reference wells can be either empty, filled with media only, or filled with media plus a substance representative of sample. A signal from the reference well or wells is measured and recorded at the beginning of the assay and again at the end. Any drift in the biosensor's properties or changes in the media solution's refractive index over the assay time can then be determined and used to determine compensated measurements from the sample wells in that microplate.

Therefore, the invention provides a microplate biosensor apparatus comprising biosensors. The apparatus includes a plurality of wells, a surface of each well including (a) a biosensor area that produces a composite signal corresponding to a target molecule and a reference sample, wherein a relatively higher proportion of the biosensor area signal corresponds to the target molecule, and (b) a reference sensor area that produces a composite signal corresponding to the target molecule and the reference sample, wherein a relatively higher proportion the reference area signal corresponds to the reference sample.

The invention provides an optical biosensor measuring apparatus. The apparatus includes (a) locating means for locating optical biosensor structures in a microplate; (b) reading means for interrogating the located optical biosensors; and (c) reference sensor means for measuring the refractive index of reference sample in the wells of the microplate. In an embodiment, the apparatus also includes transport means for moving any of the reading means, the reference sensor or the microplate structure to allow each well of the microplate structure to be addressed by the reading means and the reference sensor.

Further provided by the invention is a method for compensating for changes in the optical properties of reference sample and sensors during an optical biosensor assay. The method involves (a) contacting one or more wells of a biosensor microplate with reference sample; (b) determining a first biosensor reference signal from a well containing reference sample only; (c) adding one or more samples to the remaining wells in the microplate; (d) allowing the sample to incubate to the desired state; (e) determining a second biosensor reference signal from the well containing reference sample only; (f) determining a biosensor assay signal from one or more sample wells; and (g) determining corrected values of the assay signals based on the difference between the first and the second reference signals.

An apparatus of the invention can contain one or more optical biosensors incorporated into common assay sample carriers, such as microplates and microarray substrates. Microplates are two-dimensional matrices of liquid-containing wells, where the geometry is specified by a standard published by the Society of Biological Screening (SBS). Microplates most often comprise 24, 96, 384, or 1536 wells arranged in a rectangular matrix. Microarray substrates are planar elements upon which arrays of many different compounds are deposited, each compound most often being a member of a specific binding pair or a sample. Microarray substrates are commonly fabricated in the form of microscope slides, although other sizes and shapes are also used.

Figure 4:
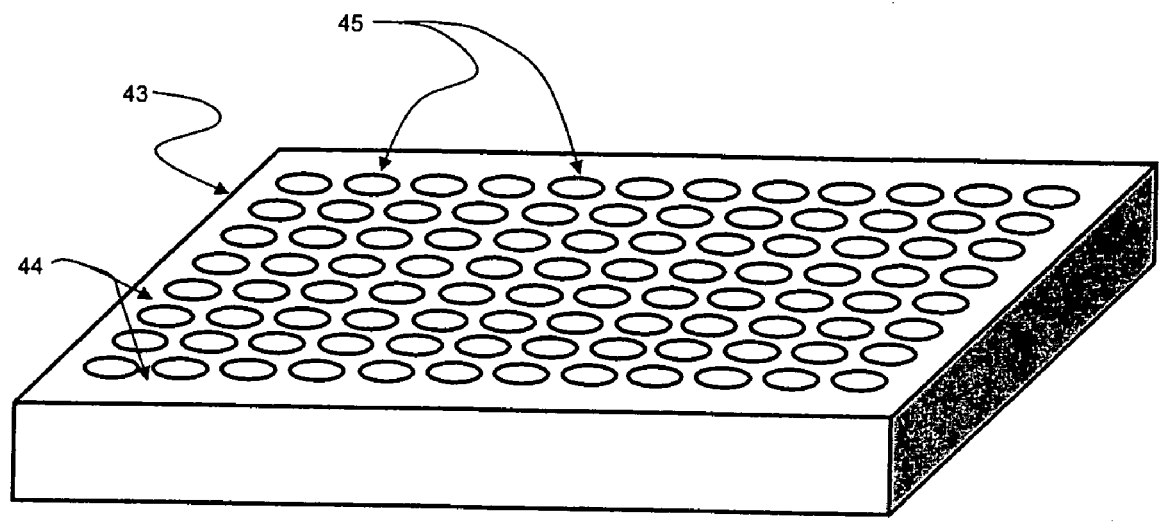
FIG. 4 shows a schematic drawing of a 96-well microplate incorporating a reference sensor according to the present invention.
Figure 4:
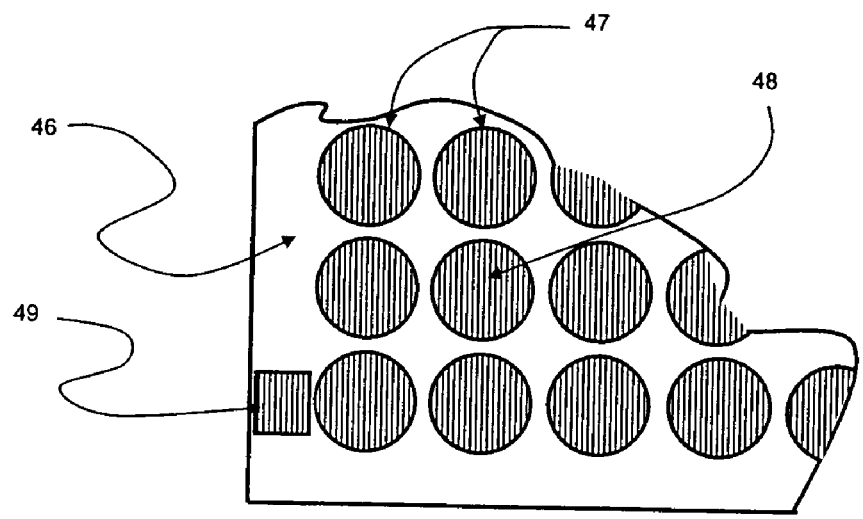

FIG. 4 shows a microplate biosensor apparatus in which a reference biosensor incorporated into a 96-well microplate or plate. As would be recognized by those skilled in the art, the principles of this apparatus apply to any well count.

In the top-oblique view of a microplate in FIG. 4a, the 96-well microplate 43 has wells 45 arranged in 8 rows and 12 columns. The well area is surrounded by a skirt area 44, which provides the microplate with structure and stiffness for handling.

In the bottom detail view of FIG. 4b, a biosensor is shown to be present in a corner of the microplate. Wells 47 have gratings 48, such as would be appropriate for a resonant calorimetric biosensor, incorporated in the well bottoms. A reference biosensor 49 is shown in the skirt area of the microplate, outside the matrix of well rows and columns. This reference biosensor is by definition not exposed to assay reagents as it is not part of a well. It can be made of an environmentally stable material as described above, providing a stable calibration reference if the well biosensors are made of a less stable material, for reasons of cost for example.

Biosensors can provide a continuous signal throughout all steps of an assay. This characteristic allows the kinetics of binding or other assay reactions to be monitored, characterized or measured. It is a further aspect of the present invention to apply controlled agitation to a sample during the assay while the biosensor or sensors are being monitored or sampled, allowing comparative kinetic measurements to be made on a plurality of samples. As an exemplary set-up for agitation of a sample during biosensor assay, an assay container that can be agitated with a mixing element has a biosensor on its top surface. The action of the mixing mechanism causes the liquid media and sample to wet the biosensor surface. When the mixing mechanism is deactivated, the liquid falls away from the biosensor surface. The biosensor can be read only when the mixer is off and the media liquid is not in contact with it. In this manner only the molecules bound to the sensor as a result of the assay reaction are sensed and changes in the media are not detected by the sensor. Agitation can be induced by a variety of well known methods, such as insertion of a rotating or reciprocating element into the reaction vessel, by the imposition of acoustic energy, by the repetitive deformation of the assay container's walls, and by the rotational or reciprocating motion of the entire assay container.

Grating-based optical biosensors, such as resonant reflective biosensors, couple light of a specific wavelength into their gratings. When interrogated with light that includes other wavelengths the non-coupled light is transmitted through the grating. It is an aspect of the present invention to use this non-coupled transmitted light to measure the optical transmittance or absorbance of the media above the biosensor at one or more wavelengths. This can be implemented by placing wavelength selecting means, such as an optical bandpass filter with a passband within the wavelength range of the interrogating light but not overlapping with the biosensor wavelength, and a light detector above the assay vessel. Changes in media plus sample transmittance or absorbance over the course of the assay can be monitored and the results can be used to differentiate media effects from binding effects in the assay.

It is another aspect of the present invention to interrogate resonant reflective optical biosensors with two orthogonal linear polarizations of light. The two different polarizations propagate differently in the biosensor and generate different signals. When the molecules at or near the surface of the biosensor are oriented linear long-chain molecules the difference in signals is pronounced. The present invention can thus be used in this way to distinguish between bound oriented long-chain molecules such as some types of proteins or nucleic acids and other molecules. These differences in signals can indicate the structure of the bound molecules. The differences can also be used to distinguish specifically-bound molecules from those bound non-specifically or to distinguish media effects from bound molecule effects.

Therefore, the invention provides a method for obtaining two measurements from a single location on a resonant reflective biosensor wherein the biosensor is interrogated with light of each of two orthogonal linear polarizations. In one embodiment, the two measurements are used to determine binding of a target molecule to the biosensor.

In addition, the invention provides an apparatus for obtaining measurements from a resonant reflective biosensor. The apparatus includes a reading means that can interrogate the biosensor with light at each of two orthogonal linear polarizations.

In the methods of the invention, it is desirable to use media with minimum polarization effects when interrogating optical biosensors with two polarizations of light. Minimizing the use of long chain molecules in media formulation or breaking up long molecules after formulation can be advantageous. It is generally desirable to formulate optical biosensor media with minimum viscosity and minimum refractive index as well.

The invention provides a method for measuring the optical absorbance of the sample and reference sample in a resonant reflective biosensor. The method involves (a) interrogating the biosensor with broadband light; (b) reading the reflected biosensor signal at a first band of resonance wavelengths with first reading means; (c) placing wavelength selecting means in the path of the transmitted broadband light, the selecting means configured to pass a second transmitted wavelength band that does not coincide with the resonant reflective band; (d) reading the relative power of the second band with second reading means; and (e) determining the optical absorbance of the sample and reference sample at the second wavelength band.

In an exemplary procedure for performing this method, the first measurement is standard resonant reflective biosensor, described above. The second is interrogating with a beam with a range of wavelengths relatively far away from the first, say between 0.1 and 0.8× or between 1.2× and 5× the nominal resonant reflective wavelength. The light at this second band of wavelengths will pass through the biosensor and through the liquid sample above it. A light power detector, such as a photodiode or a spectrometer, is placed to intercept the light passing through the sample. The optical transmission characteristics of the sample measured thereby provide additional data as to the sample's composition and state.

The invention also provides a method for improving the spectral peak resolution of a resonant reflective biosensor. The method involves (a) determining two or more reference spectra from a sample quantity of biosensors on a high-resolution spectrometer; (b) characterizing the reference spectra with an algorithm or equation; (c) obtaining one or more assay spectra from a biosensor using a low-resolution spectrometer; and (d) determining reflectance spectrum peaks of the assay spectra by interpolating along the curve defined by the algorithm or equation.

Further provided by the invention is method of interrogating a resonant reflective biosensor at two wavelengths. In the method, a first wavelength generates a signal relatively more sensitive to a target molecule and a second wavelength generates a signal relatively more sensitive to the reference sample.

For a grating-based resonant reflective biosensor, for example, the resonant effect can be produced at two different wavelengths by superimposing two different grating frequencies. The effect can also be produced by one grating with two beams at different incidence angles, or by beams a factor of two different in wavelength. The longer wavelength interrogation light generates an evanescent sensing wave with a deeper penetration depth, relatively more sensitive to the refractive index of the buffer or media. The shorter wavelength interrogation light generates an evanescent sensing wave with a shorter penetration depth, relatively more sensitive to the binding assay at the surface. The signals generated by the two wavelengths can be analyzed together to reduce the effect of changes in the refractive index of the media.

Generally, undesired media effects on measurements from optical biosensors can be corrected by assaying "blank" samples: measuring the signals from biosensors exposed to reference sample only. These measurements must be performed anew on each new batch of media and often both at the beginning and end of the assay. In an aspect of the present invention, the refractive index of reference sample is measured and recorded before it is used in assays. This eliminates the use of a relatively expensive biosensor to perform a calibration function in parallel with every assay when that function can be performed in advance. The index of reference sample (media) can be measured at several temperatures over the range used in assays. The media's refractive index can be marked on its container in human-readable or machine-readable form such as barcodes and the like. When marked in machine-readable form the media's properties can be transferred in a simple and robust manner to a computer controlling or monitoring the assay reading instrument where signal correction calculations can be performed.

A variety of media formulations can be used in a method of the invention. In one aspect of the invention, biosensor assay media containing water-miscible organic solvents as an alternative to aqueous media are provided. Media of this type are capable of dissolving hydrophobic compounds, including hydrophobic proteins which are increasingly studied as potential disease markers or drug targets. Label-less detection is particularly advantageous for use with these solvents as many fluorescent labels (e.g. TRITC) have poor performance or uncharacterized performance in non-aqueous environments. Therefore, the invention provides a method for performing label-less assays on hydrophobic compounds using an optical biosensor wherein the reference sample comprises a water-miscible organic solvent. Such hydrophobic compounds can be, for example, hydrophobic proteins.

A variety of assays can be performed using an apparatus or method of the invention. One common type of assay is a specific binding assay in which one of the specific binding pair members is immobilized on a solid support. A solution of sample in media is brought into contact with the immobilized binding pair member. If the complementary binding pair member is a constituent of the sample, a fraction of the members in solution will bind to their complementary immobilized binding pair partners. The assay measurement is then performed on the surface upon which the specific binding pairs have been immobilized.

A member of a specific binding pair can be a target molecule to be detected in a method of the invention. Exemplary specific binding pairs include antibodies with antigens, strands of complementary nucleic acids with one another, receptors with ligands and the like as a means of detecting or measuring one of the specific binding pair members in solution.

Non-limiting examples of immune specific binding pairs include antigen/antibody binding pairs and hapten/antihapten binding pairs. The term antibody is intended to include polyclonal and monoclonal antibodies as well as antigen-binding fragments thereof. Fab-type fragments are antibody fragments devoid of the Fc portion, e.g., Fab, Fab' and F(ab')2 fragments, or can be so-called "half-molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, ligands-receptors, lectins-sugars, etc.

A variety of labels can be used to generate an assay signal, if desired. A label is a detectable substance such as a radioactive isotope, chromogenic dyes, fluorophores or the like that are chemically bonded to either or both of the members of specific binding pairs prior to the assay. Label molecules generate signals and are chosen to allow detection instruments to detect or measure the binding events between the binding pair members. A significant disadvantage of labels is that their presence can affect the binding between the members of binding pairs so that the binding measured from signals generated by labeled binding pairs can not correlate exactly with the binding of non-labeled species.

Assays can be performed without labels and the results can be detected or measured using various techniques of label-less detection and measurement. Label-less assays are performed on or in close proximity to devices called biosensors. Biosensors typically generate a signal from changes of the thickness, density, or optical properties of molecules that bind to a sensing surface. Optical biosensors, in particular, detect changes in the composite refractive index of the substances within a distance of a fraction of a wavelength from their sensing surfaces. For binding assays the sensing surface typically has immobilized members of specific binding pairs attached to it. For functional assays, cells, cell fragments, enzymes or enzyme substrates etc. can be immobilized on the biosensor surface.

A variety of samples can be used in a method or apparatus of the invention. Samples are typically mixtures of unknown or varying composition derived from biological sources such as blood, tissue, cells, and the like. In functional assays samples are generally known compounds, such as a compound that binds to a biological entity. Samples in functional assays can also be substances such as enzymes that have activity themselves. A sample useful in a method of the invention is generally dissolved or suspended in media, where the media allows the sample molecules to diffuse with sufficient mobility to allow them to participate in an assay reaction. Media is often an aqueous saline buffer mixture but can also be other aqueous or non-aqueous solutions or mixtures, as is described herein above.

The use of curve fitting, correlation, and the like is known in the processing of spectral signals from resonant reflective biosensors for the purpose of reducing noise in the spectrum data. It is an aspect of the present invention to use high-resolution spectral data, generated on a high-resolution reading instrument, to characterize biosensor spectra. The measured high-resolution spectra are then reduced to an equation or algorithm, such as by curve-fitting, and the resulting curve or algorithm is used to improve data from low-resolution reading instruments. The high-resolution instrument, which can be of higher cost or more difficult to use than is practical for a commercial assay instrument, is used on a sampling basis to characterize samples of biosensors. Lower-resolution instruments are then used by researchers to take assay measurements using biosensors from the sampled batches. The spectral resolution of the lower-resolution instruments is improved by utilizing the spectrum curve or algorithm as an input to data processing.

A biosensor can be used to detect target nucleic acids. Therefore, the invention provides an apparatus for performing real-time detection of an amplified target nucleic acid. The apparatus includes (a) a capillary tube; (b) temperature control means that controls the temperature of three of more segments of the capillary tube wherein each segment contains zones maintained at three or more selected temperatures; (c) means for moving a sample to the various temperature zones; and (d) a biosensor configured to measure the amount of nucleic acid in the sample. In an embodiment, the biosensor is an optical biosensor. In another embodiment, the capillary is formed into a serpentine shape comprising a serially connected plurality of repeated elements, each element having three or more temperature-controlled zones and a biosensor.

Accordingly, the invention provides a method of determining an amount of a target nucleic acid. The method involves (a) introducing a sample into a capillary tube, the sample suspected of containing a target nucleic acid, wherein the sample comprises a polymerase enzyme, one or more primers and nucleotides; (b) controlling the temperature of three of more segments of the capillary tube wherein each segment contains zones maintained at three or more selected temperatures; (c) moving the sample through the tube, whereby the target nucleic acid, if present, is amplified by the polymerase enzyme; and (d) determining an amount of the target nucleic acid using a biosensor. In one embodiment, the capillary tube has a serpentine shape comprising a serially connected plurality of repeated elements, each element comprising three temperature-controlled zones and a biosensor.

Exemplary means for moving a sample to the various temperature zones include applying air at a controlled pressure to an end of the capillary for a controlled length of time, the pressure and time having been previously correlated with movement of a bolus of liquid.

An amount of the target nucleic acid can be determined using a biosensor, for example, by immobilizing a complementary single-strand to the biosensor surface and allowing hybridization. Hybridization is a standard binding signal that is sensed by a wide variety of biosensors including SPR, colorimetric resonant reflection, interfeometry, and the like.

An exemplary procedure and apparatus for performing real-time detection of an amplified target nucleic acid is as follows:

First, the sample containing or suspected of containing the target nucleic acid, nucleotides, primers, and polymerase enzyme are introduced as a small volume into a capillary tube (FIG. 1, 1). Typical volumes are in the range of 0.1 to 5 microliters, and the assay media forms a bolus of liquid (2) in the tube with air or another inert gas or an inert liquid on each side of it. The tube is divided into three temperature-controlled zones (3, 4, 5) with temperature transition zones (6, 7) between them. The volume of the liquid bolus is such that it is largely confined to only one zone at a time. Controlled temperatures T1, T2 and T3 are applied to three zones of the tube, where T1 is the denaturing temperature, T2 is the annealing temperature, and T3 is the polymerizing temperature for the nucleic acid target. The volume of the bolus of sample and the cross-sectional area of the capillary are selected such that the extent of the sample bolus is largely confined within each temperature zone. Controlled volumes of air (8, 9) or another inert gas are admitted to either end of the capillary to drive the bolus from one temperature zone to another. Within each zone it is allowed to incubate for sufficient time for the molecular processing associated with the zone to proceed to substantial completion. A biosensor (10), such as an optical biosensor, is integrated into the end of the capillary adjacent to the T3 zone to measure the concentration of amplified product. A subsequent amplification cycle can then be initiated by admitting a controlled volume of inert fluid (9) to drive the bolus of liquid back to the T1 zone. Cycles can be repeated until the population of amplified products is sufficient to extrapolate the starting concentration.

Figure 2:
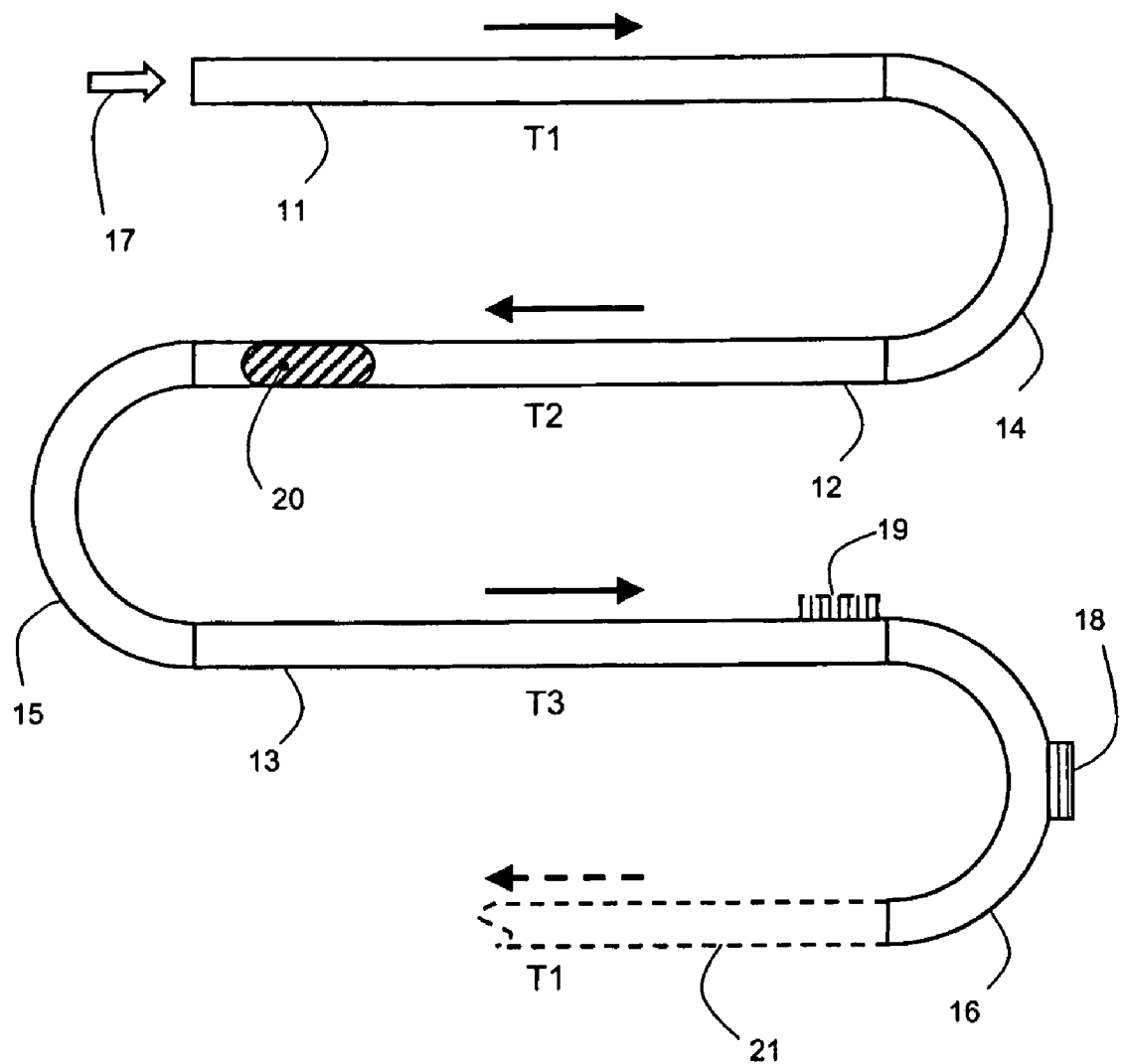
FIG. 2 shows a schematic drawing of one embodiment of an apparatus for performing real-time detection of an amplified target nucleic acid in which the capillary is formed into a serpentine shape.

In an alternate configuration the capillary tube is significantly extended and formed into a serpentine shape (FIG. 2), with multiple periods of continuous three-component "s"-shaped elements. The "s" shaped elements comprise three substantially linear transverse sections in the middle (11, 12, 13) and three curved turnaround sections on each of the two ends of the linear sections (14, 15, 16). An element comprising a set of 3 of these components subjected to a specific set of localized temperature controls supports one cycle of the nucleic acid amplification process. The first component of a second element (21) is shown in dotted lines in FIG. 2. Multiple elements would be joined together in series to perform multiple amplification cycles, one element per amplification cycle.

Each element of serpentine tubes is placed in a thermal environment such that each of the three linear sections is maintained at one of three temperatures. The first linear section is maintained at a first controlled temperature T1, the second at T2 and the third linear section at a third controlled temperature T3. The transition zones in the curved turnarounds between the transverse sections exhibit the interzone temperature differences as gradients along a transition length. Air or another inert gas (17) is introduced into the tube at a controlled flowrate to advance the bolus of liquid sample (20) through the capillary at a controlled velocity. A biosensor, most advantageously an optical biosensor, is integrated into the turnaround downstream of the T3 zone (18). Alternately the biosensor is integrated into the end of the straight capillary at the end of or adjacent to the T3 zone (19). The refractive index of the sample liquid changes as the concentration of free nucleotides drops and the concentration of polymerized nucleic increases after each progressive advance of the sample bolus through the varying temperature zones, performing an amplification cycle. In this manner the biosensors can measure the incremental increases in polymerized nucleic acid concentration after each cycle, the results of which can be extrapolated back to calculate the initial concentration of the target nucleic acid in the sample.

Real-time detection of amplified nucleic acid targets using fluorescent labels has been described in U.S. Pat. Nos. 5,210, 015 and 5,994,056, which are incorporated herein by reference.

Although aspects of the present invention have been described by particular embodiments exemplified herein, the present invention is not so limited.

What is claimed is:

1. A method for interrogating at least one biosensor, the method comprising:
    contacting one or more wells of a microplate with a reference sample,
    determining a first reference measurement from a well containing only the reference sample by interrogating the at least one biosensor associated with said well,
    adding one or more samples to at least one of the remaining wells in the microplate,
    allowing the samples to incubate,
    determining a second reference measurement from the well containing only the reference sample by interrogating the at least one biosensor associated with said well,
    generating at least one sample measurement by interrogating the at least one biosensor associated with the at least one remaining well, and,
    determining a corrected measurement based on a comparison of the reference measurements and the at least one sample measurement.

2. A method according to claim 1, where generating at least one sample measurement includes:
    imaging a field of interest on at least one of the at least one biosensor to provide an image,
    determining planar coordinates of locations of interest in the image, and, interrogating the at least one biosensor at the locations of interest.

3. A method according to claim 2, where imaging a field includes detecting at least one of: diffuse reflection, contrasting color, light transmission, light absorption, light scatter, fluorescence, and chemiluminescence.

4. A method according to claim 2, where the field of interest is larger than the locations of interest.

5. A method according to claim 1, where the at least one biosensor is substantially planar.

6. A method according to claim 1, where the at least one biosensor is moveable.

7. A method according to claim 1, where interrogating the at least one biosensor includes interrogating at least two of the at least one biosensors in parallel.

8. A method according to claim 1, where the at least one biosensor associated with the well containing only the reference sample is attached to a support structure that includes the at least one biosensor.

9. A method according to claim 8, where the support structure is a microplate.

10. A method according to claim 1, where the at least one biosensor includes at least one optical biosensor.

11. A method according to claim 1, where the at least one biosensor includes at least one microarray substrate.

12. A method according to claim 1, where:
determining a first reference measurement includes detecting a first composite signal that corresponds to a target molecule and a reference sample, with a higher proportion of the first composite signal corresponding to the target molecule relative to the reference sample, and,
determining a second reference measurement includes detecting a second composite signal that corresponds to the target molecule and the reference sample, with a higher proportion of the second composite signal corresponding to the reference sample relative to the target molecule.

13. A method according to claim 1, further comprising:
providing a sample in contact with the at least one biosensor, and,
binding an entity of known mass to an analyte contained in the sample.

14. A method according to claim 1, further comprising:
providing a sample in contact with the at least one biosensor, and, using a catalyzed reporter deposition.

15. A method according to claim 1, where generating at least one of a first reference measurement or a second reference measurement includes measuring a refractive index of a reference sample in a well of a microplate.

16. A method according to claim 1, where:
determining a corrected measurement includes determining corrected values based on a difference between the first reference measurement and the second reference measurement.

17. A method according to claim 1, further comprising:
providing a capillary tube having at least three segments,
controlling the at least three segments at three or more temperatures to create at least three temperature zones, and,
moving a sample to at least some of the at least three temperature zones,
where the at least one biosensor is configured to measure an amount of nucleic acid in the sample.

18. A method according to claim 17, where the capillary tube is formed into a serpentine shape.

19. A method according to claim 18, where the capillary tube includes a plurality of elements, where each element includes at least three temperature zones and at least one biosensor.

* * * * *